United States Patent [19]

Schröder

[11] Patent Number: 4,687,748

[45] Date of Patent: Aug. 18, 1987

[54] MAGNETIC CARBOHYDRATE PARTICLES AS CARRIERS FOR AFFINITY SEPARATION PURPOSES

[75] Inventor: Ulf Schröder, Lund, Sweden

[73] Assignee: Gambro Lundia AB, Sweden

[21] Appl. No.: 552,144

[22] PCT Filed: Mar. 23, 1983

[86] PCT No.: PCT/SE83/00106

§ 371 Date: Nov. 7, 1983

§ 102(e) Date: Nov. 7, 1983

[87] PCT Pub. No.: WO83/03426

PCT Pub. Date: Oct. 13, 1983

[30] Foreign Application Priority Data

Mar. 29, 1982 [SE] Sweden .............................. 8201972

[51] Int. Cl.$^4$ .................. G01N 33/553; G01N 33/53; G01N 33/545

[52] U.S. Cl. .................................... 436/526; 436/529; 436/530; 436/531; 435/7; 252/62.54

[58] Field of Search ............... 436/526, 529, 530, 531; 252/62.54; 435/7; 260/112 R

[56] References Cited

U.S. PATENT DOCUMENTS

| 4,115,534 | 9/1978 | Ithakissios | 424/1 |
| 4,230,685 | 10/1980 | Senyei et al. | 424/12 |
| 4,241,176 | 12/1980 | Avrameas | 435/7 |
| 4,357,259 | 11/1982 | Senyei et al. | 252/316 |
| 4,418,152 | 11/1983 | Hosaka et al. | 436/511 |
| 4,452,773 | 6/1984 | Molday | 424/1.1 |
| 4,454,234 | 6/1984 | Czerlinski | 436/526 |

OTHER PUBLICATIONS

Halling et al., Biotechnology and Bioengineering, vol. XXI, pp. 393–416, (1979).
Mosbach and Schroder, Magnetic Microspheres for Targeting of Drugs, Enzyme Engineering, vol. 5, Weetall and Royer, Eds., Plenum Publishing Corp., 1980, pp. 239–241.

Primary Examiner—Robert J. Warden
Assistant Examiner—Patricia L. DeSantis
Attorney, Agent, or Firm—Lerner, David, Littenberg, Krumholz & Mentlik

[57] ABSTRACT

Magnetically responsive spheres having an average diameter less than 1,000 nm are prepared by dissolving a carbohydrate polymer in a polar solvent, suspending magnetic material in the dissolved carbohydrate, emulsifying the suspension with an emulsion liquid to form an emulsion containing droplets of the suspension and then contacting the emulsion with a crystallizing liquid capable of crystallizing the carbohydrate polymer. The resulting spheres may be bonded with a bioabsorptive material and can be employed in processes such as cell separation, affinity purification or immunochemical assays.

10 Claims, No Drawings

MAGNETIC CARBOHYDRATE PARTICLES AS CARRIERS FOR AFFINITY SEPARATION PURPOSES

This invention relates to magnetically responsive crystalline-carbohydrate spheres or particles and to their use together with bioadsorptive materials. This includes coupling, adsorption and/or entrapment of bioadsorptive materials to said spheres or particles in connection with the use of interactions of these bioadsorptive materials with biological substances and cells. Preferably, in this invention use is made of magnetic nano-spheres.

By "magnetic nano-sphere" is meant a sphere or a particle the average diameter of which is 1–999 nm and which is responsive to a magnetic field.

The advantage of using nano-spheres instead of micro-spheres is obvious from a calculation of the ratio of available surface area to volume unit of packed spheres:

A tenfold reduction of the diameter of the sphere gives a tenfold increase of the number of surface units per volume units of packed spheres. When bioadsorptive materials are to be used for covalent coupling or adsorption onto the surface of the spheres, the effort should be to use nano-spheres since the amount of bioadsorptive materials per volume units of packed spheres is maximized. Furthermore, a nano-sphere is desirable in the following examples of separation, since the magnetic force to which for example a cell is exposed is considerably greater than in a case of a magnetic micro-sphere. This is due to the fact that a larger number of interactions is possible between nano-spheres and a cell compared to micro-spheres.

Examples of interactions which can be used in connection with the present magnetic nano-spheres are as follows:
1. protein-protein
2. protein-carbohydrate
3. protein-lipid
4. protein-hapten, hormone or other low molecular weight substances, and combinations of the above interactions.

With the use of said interactions there exists the possibility of separating heterogeneous biological material.

Examples of interactions of the above-mentioned type can be:

cell separation, wherein a combination of interactions is included, immunochemical analysis, preferably where a pure interaction of any of the types 1–4 is involved depending on the purpose of the analysis, enzyme reaction, preferably when a protein-low molecular weight substance interacts, but also the types 1–3 are applicable, and, affinity purifying, when different types of interactions can be used depending on the substance to be purified.

Different types of magnetic spheres or magnetic particles are known since long in the literature for use such as in the above-mentioned interactions. A survey of magnetic spheres as carriers for bioadsorptive material is published in Enz. Microb. Technol. Vol. 2, 1980 by Halling & Dunhill. For example, the desired characteristics which a magnetic sphere or particle should have are mentioned therein:

1. The magnetic material shall be resistant to corrosion in aqueous surroundings.
2. The polymer as such shall be chemically inert.
3. Bioadsorptive materials shall be able to couple or adsorb in a stable way to the surface of the microsphere.
4. The sphere shall, most preferably, be less than 1 $\mu$m.
5. The sphere shall contain enough magnetic material.
6. The spheres must not aggregate irreversibly at repeated treatment in a magnetic field.

A number of different magnetic materials are described and commercially available, such as $Fe_3O_4$, Ni-NiO, Ni-TiO$_4$, Mn-Zn ferrite, Ni etc. Generally, magnetite ($Fe_3O_4$) is used, since it is readily available and is not oxidized in aqueous surroundings.

Useful polymer materials are for example acrylic derivative, agarose, proteins, copolymers of acryl and agarose, starch and cellulose. Among these neither starch nor proteins meet with the requirement of being chemically inert or resistant to degrading.

Known methods for producing magnetic microspheres are in general emulsion polymerizations with simultaneous cross-linking of the polymer to obtain stable microspheres. In one case the stabilization is obtained through heat-denaturation of protein (U.S. Pat. No. 4,230,685). As polymer albumin (J. Pharm. Sci (1981) 70, 387–389) or different acrylic derivatives (Nature (1977) 268, 437–438 or Science (1978) 200, 1074–1076) are used. The magnetic material is $Fe_3O_4$. Various methods for coupling, adsorption or entrapment of the bioadsorptive material to/in the polymer are described in the literature and reference is made to Methods in Enzymology, vol. 44 (1976) (K. Mosbach).

A method for producing starch micro-spheres in which the magnetic material is entrapped (FEBS Lett. (1979) 102, 112–116) has been described. However, this known technique is not applicable in the present invention, since the obtained magnetic spheres are too large (2–3 microns) and are oxidized very quickly in aqueous surroundings due to the fact that the magnetic material is pure iron.

This problem can be avoided in a simple way according to the present invention, whereby magnetically responsive carbohydrate nano-spheres being resistant to corrosion can be produced.

DESCRIPTION OF INVENTION

The invention relates to preparation and use of magnetically responsive spheres having an average diameter of 50–900 nm and being built up of a polymer matrix in which magnetic particles having a diameter of 10–20 nm have been included.

More particularly, the present invention relates to the preparation and use of magnetically responsive spheres having an average particle diameter of up to about 1,000 nanometers (nm), and in which the particles are built up of crystalline carbohydrate polymers. The magnetically responsive particles are intended to include bioadsorptive materials bonded thereto, such as antibodies, for cell separations and the like.

In accordance with another aspect of this invention, cells, or other substances in biological fluids such as blood are separated by means of these magnetically responsive particles with bioadsorptive materials thereon by causing the biological fluids, together with these particles, to flow continuously through a tube, and by providing a magnetic field which is created by magnets surrounding the tube, so that the particles with the captured cells, etc., can be collected and retained within the tube while remaining fractions of fluid freely pass therethrough. Once again, in this embodiment of the invention the particles are produced from crystalline carbohydrate polymers containing these magnetic materials having an average diameter from about 1 to 1,000 nm, and preferably from about 10 to 20 nm.

According to the present invention it is possible to prepare magnetically responsive carbohydrate spheres having a diameter of 50–900 nm. Thereby is obtained a large surface area per volume unit of packed spheres such that the possibilities of coupling of biological substances is essentially higher than with other types of carbohydrate spheres (e.g. Sephadex® or Sepharose®). Due to the fact that the biological material is coupled to the surface of the spheres a more rapid reaction is also obtained since the diffusion barriers, occurring in a 200 micron sphere, are completely eliminated.

The matrix material in the preparation of the magnetic nano-spheres according to the invention is a carbohydrate polymer. According to the present invention use is made of the following carbohydrate polymers, dextran, pullulan, glycogen, starch, cellulose, agarose, alginate, chitosan or carrageenan. Dextran, cellulose and agarose are preferred and are used mainly since they are biochemically well characterized and inert in most biological systems. There is also the possibility of modifying carbohydrate polymers with for example acetyl, hydroxypropyl, propionyl, hydroxyethyl-hydroxypropanoyl, different derivatives of acrylic acid or similar substituents.

The present process relates to preparation of magnetic spheres having an average diameter of 50–900 nm. The process is characterized in that the carbohydrate polymer is dissolved in a solvent having a high dielectric constant to a concentration normally within the range of 0.1–150% (w/v). Useful examples of such solvents are inter alia dimethylformamide, ethylene glycol, sulfolane, dimethyl sulfoxide, propylene carbonate, water and formamide or mixture of these. The magnetic material is suspended in the dissolved carbohydrate polymer. The magnetic material consists of magnetite ($Fe_3O_4$) having a size of 10–20 nm. A method for preparation of such small particles is known and these are commercially available via Ferrofluid Corp., U.S.A. Other useful magnetic materials include particles or colloids having a main content of aluminum, nickel, cobalt, copper, silver, manganese or platina.

The so obtained suspension of magnetic material in the dissolved carbohydrate polymer is emulsified in an emulsion system consisting of said magnet suspension and an emulsion medium consisting of a liquid which is immiscible with said magnet suspension. A further characteristic of the liquid is that it participates in the formation of small drops of magnet suspension in the emulsion medium.

Examples of useful emulsion media may be vegetabilic oils, preferably rape-oil or maize-oil, and other useful hydrophobic emulsion media include paraffin oils or silicon oils.

Another type of emulsion medium comprises organic solvents in which one or more emulsifiers have been dissolved. Useful such organic solvents comprise inter alia xylene, toluene, ethyl benzene, diethyle benzene, propyl benzene, ethylene chloride and other similar solvents and mixtures thereof.

In order to emulsify the emulsion sonicates or a high-pressure homogenizer are used. The obtained emulsion, in which the carbohydrate magnetite suspension is emulsified in form of drops, is stabilized by transferring same into a liquid the characterisric of which is that it can crystallize the carbohydrate polymer, whereby the magnetic material is enclosed.

Useful such liquids are ethanol, methanol and acetone, preferably acetone. After crystallization the nano-spheres are further washed with acetone. Drying can be realized in a simple way through rotatory evaporation or air-drying.

The present invention furthermore relates to covalently coupling of bioadsorptive materials onto the surface of the magnetic nano-sphere.

EXAMPLE 1

0.45 g dextran, having a molecular weight of 40,000 (Pharmacia AB, Uppsala), was dissolved through warming in a mixture consisting of 700 µl $H_2O$ and 300 µl Ferrofluid (EMG 806,200 Gauss, Ferrofluid Co., U.S.A.). The solution was allowed to cool to room temperature, whereafter it was transferred into a 100 ml beaker containing 25 ml cold (+4° C.) vegetabilic oil. The mixture was emulsified with ultrasonic (Ultrasonic 350 G) for 1 minute, whereafter the obtained emulsion was poured into 200 ml acetone, in which the emulsifier Tween 80® has been dissolved to a concentration of 0.1% (w/v). While thoroughly pouring the emulsion into acetone-Tween 80 it was stirred at about 1000 rpm. The crystallized magnetic nano-spheres were washed 4 times with said acetone solution, whereafter they were air-dried.

EXAMPLE 2

The same procedure as in example 1 was followed, except for the use of 150 mg magnetite particles (EMG 1111) instead of 300 µl Ferrofluid.

EXAMPLE 3

The same procedure as in example 1 was followed, except for the use of xylene with the emulsifiers Gafac PE-520 and Tween 80, both with a concentration of 5% (w/v), instead of the vegetabilic oil.

EXAMPLE 4

The same procedure as in example 1 was followed, except for the fact that the dextran was crystallized in ethanol with addition of 1 g Tween 80 per liter ethanol instead of acetone-Tween 80.

EXAMPLE 5

The same procedure as in example 1 was followed, except for the fact that 0,3 g starch was dissolved in 700 µl formamide and 300 ml Ferrofluid (EMG 2111) instead of dextran in $H_2O$.

EXAMPLE 6

The same procedure as in example 1 was followed, except for the fact that dextran having a molecular weight of 500,000 instead of 40,000 was used.

EXAMPLE 7

The same procedure as in example 1 was followed, except for the fact that 0.8 g 2% agarose or carrageenan was mixed with 300 µl Ferrofluid at a temperature of +50° C. instead of dissolving the dextran in water and Ferrofluid.

EXAMPLE 8

The same procedure as in example 1 was followed, except for the fact that 0.8 g 2% alginate instead of dextran and water was mixed with 300 µl Ferrofluid and emulsified in the vegetabilic oil containing 0.1% (w/v) of the emulsifier Gafac RM-410 instead of pure oil.

EXAMPLE 9

The same procedure as in example 1 was followed, except for the fact that 0.8 g 1% chitosan, dissolved at pH 5, was mixed with 300 µl Ferrofluid instead of dextran, water and Ferrofluid.

EXAMPLE 10

The same procedure as in example 1 was followed, except for the fact that 3 g α-cellulose was dissolved in 150 g N-ethylpyridine chloride and 75 g dimethylformamide, and 0.8 g of this solution was mixed with 300 µl Ferrofluid instead of dextran, water and Ferrofluid.

EXAMPLE 11

25 g of the nano-spheres obtained in example 1, activated with tresylchloride, was suspended in 1 ml 10 mM phosphate buffer, pH 7.2, containing 0.9% NaCl, whereafter 20 mg labled (fluoroscein) bovine serum albumin (BSA*) was added. The protein was coupled during 15 minutes at room temperature and was compared with the case where the nano-spheres were dissolved directly in phosphate buffer containing BSA*. Non-coupled BSA* was washed (3 times) off with phosphate buffer; the nano-spheres were kept stationary by means of a small hand magnet. After washing the result was checked by means of a Niko fluorescence microscope and it was established that all nano-spheres were fluorescing strongly and no difference between the two ways of coupling was detected.

EXAMPLE 12

The magnetic nano-spheres were activated with bromocyanide (60 mg BrCN/gr wet gel) at pH 10.75 during 11-12 minutes. 500 µl anti-alphafetoprotein-antibodies were coupled to the gel over night at +4° C.

This magnetic antibody-gel was used to measure the serum level on alphafetoprotein (AFP) by means of a so-called sandwich-ELISA. Thus, after mixing the nano-spheres with test serum and incubation for 2 hours, the spheres were washed by applying small hand magnets outside the test tubes containing serum sample and spheres, whereafter the wash buffer was discarded. The washing procedure took 5-10 minutes. Thereafter anti-AFP conjugated to glucose oxidase was added. After 2 hours of incubation and following washing the enzyme substrate was added and the colour reaction was followed by a photometer after 30 minutes. This sandwich enzyme immunoassay gives a standard curve in which the absorbance is proportional to the amounts of AFP in the sample. The assay time was about 5 hours, the sensitivity 10-50 ng AFP/ml sample, and the test capacity was about 100 samples/day.

EXAMPLE 13

5 mg magnetic nano-spheres according to example 1, activated with tresylchloride, were suspended in 300 µl phosphate buffer, pH 7.2, containing 0.9% NaCl and 25 µl goat anti-mouse IgG (49.8 mg/ml). The suspension was incubated for 30 minutes at room temperature and washed with phosphate buffer 3 times by means of a magnet which held the spheres in place. After washing the spheres were resuspended in 0.5 ml phosphate buffer, pH 7.2, containing 0.5% NaCl. To this were added $10^7$ human peripherial lymphocytes, pre-incubated with monoclonal antibodies of anti-OKT4 specificity (OKT4 is a marker of a T-cell).

The cell and sphere suspension was incubated for 60 minutes at 37° C., whereafter the test tube was exposed to a magnetic field. Cells coated with the magnetic nano-spheres were held stationary by the magnet, and the cells were washed twice with phosphate buffer. The separated cell population was about 40% of added lymphocytes and no (<1%) contamination of non-OKT4 positive cells could be detected.

EXAMPLE 14

To 5 mg magnetic nano-spheres, activated with tresylchloride, were coupled a carbon hydrate-binding protein. This lectine, phytohemaglutine (PHA), binds to hydrate residues on cell surfaces or free in solution. PHA positive magnetic spheres (0.5 mg/g wet gel) were incubated with red blood corpuscles (RBC) from rabbit for 60 minutes at 25° C. The suspension was pumped in a tube exposed to a magnetic field of about 3000 gauss, whereby RBC was retained where the tube passed the magnetic field. This shows that even relatively weak interactions of the type lectine-carbon hydrate, association constants are about $10^4 - 10^5 M^{-1}$, can be used for cell separation. When magnetic nano-spheres were used very little contamination of non-bonded cells is obtained in the outflow for reasons already discussed.

I claim:

1. A method for preparing magnetically responsive spheres comprising the steps of dissolving a carbohydrate polymer in a polar solvent therefor so as to obtain a dissolved carbohydrate; suspending magnetic material in said dissolved carbohydrate so as to obtain a suspension of magnetic material in said dissolved carbohydrate; emulsifying said suspension with an emulsion liquid which is immiscible with said suspension so as to form an emulsion containing droplets of said suspension in said emulsion liquid; stabilizing said emulsion by contacting said emulsion with a crystallizing liquid different than said polar solvent so as to thereby crystallize said carbohydrate polymer so as to enclose said magnetic material in spheres of said carbohydrate polymer having an average diameter of less than 1,000 nm; and separating said spheres therefrom.

2. A method according to claim 1, wherein the separated spheres are washed and dried.

3. A method according to claim 1, wherein the carbohydrate polymer is selected from the group consisting of starch, glycogen, pullulan, dextran, cellulose, agarose, alginate, chitosan, and carrageenan, and derivatives thereof.

4. A method according to claim 1, wherein the crystalline magnetic responsive particles are bonded with bioadsorptive material.

5. A method according to claim 4, where said bonded bioadsorptive material is an antibody.

6. A method according to claim 1 wherein said magnetic material includes a metal selected from the group consisting of Fe, Al, Ni, Co, Cu, Ag, Mn, and Pt.

7. The method of claim 6 wherein said magnetic material is in the form of particles having an average diameter of 1 to 1,000 nm.

8. A method according to claim 7 wherein the magnetic material is in the form of particles having an average diameter of between 10 and 20 nm.

9. A method for preparing magnetically responsive spheres comprising the steps of dissolving a carbohydrate polymer in a polar solvent therefor so as to obtain a dissolved carbohydrate; suspending magnetic material in said dissolved carbohydrate so as to obtain a suspension of magnetic material in said dissolved carbohydrate; emulsifying said suspension with an emulsion liquid which is immiscible with said suspension so as to form an emulsion containing droplets of said suspension in said emulsion liquid; stabilizing said emulsion by contacting said emulsion with a crystallizing liquid different than said polar solvent to thereby crystallize said carbohydrate polymer so as to enclose said magnetic material in spheres of said carbohydrate polymer having an average diameter of less than 1,000 nm; and separating said spheres therefrom, said crystallizing liquid being selected from the group consisting of ethanol, methanol, acetone and derivatives thereof.

10. A method according to claim 9 wherein said crystallizing liquid is acetone.

* * * * *

UNITED STATES PATENT AND TRADEMARK OFFICE
CERTIFICATE OF CORRECTION

PATENT NO. : 4,687,748
DATED : August 18, 1987
INVENTOR(S) : Schroder, et al

It is certified that error appears in the above-identified patent and that said Letters Patent is hereby corrected as shown below: Title page:

In the identification of inventors, add
 --Carl Borrebaeck, Lund, Sweden--

Delete "[73] Assignee: Gambro Lundia AB, Sweden"

Signed and Sealed this

Thirty-first Day of May, 1988

Attest:

DONALD J. QUIGG

*Attesting Officer*   *Commissioner of Patents and Trademarks*